United States Patent
Fenton (10) Patent No.: US 8,292,902 B2
(45) Date of Patent: Oct. 23, 2012

(54) DOUBLE ROW FIXATION SYSTEM, MEDIAL ROW ANCHOR PLACEMENT SYSTEM

(75) Inventor: Paul Fenton, Marblehead, MA (US)

(73) Assignee: Tornier, Inc., Edina, MN (US)

( * ) Notice: Subject to any disclaimer, the term of this patent is extended or adjusted under 35 U.S.C. 154(b) by 1124 days.

(21) Appl. No.: 12/146,350

(22) Filed: Jun. 25, 2008

(65) Prior Publication Data

US 2009/0138002 A1    May 28, 2009

Related U.S. Application Data (60) Provisional application No. 60/946,012, filed on Jun. 25, 2007.

(51) Int. Cl.
*A61B 17/10* (2006.01)
(52) U.S. Cl. .......................................... 606/139; 606/28
(58) Field of Classification Search ................. 606/139, 606/28, 148, 232, 107, 205, 207, 142, 74, 606/213, 144, 143
See application file for complete search history.

(56) References Cited

U.S. PATENT DOCUMENTS

| | | | | |
|---|---|---|---|---|
| 2,631,585 A * | 3/1953 | Siebrandt | ..................... | 606/86 R |
| 5,575,801 A | 11/1996 | Habermeyer et al. | | |
| 5,697,933 A * | 12/1997 | Gundlapalli et al. | ........... | 606/96 |
| 5,893,880 A | 4/1999 | Egan et al. | | |
| 5,964,765 A | 10/1999 | Fenton, Jr. et al. | | |
| 5,968,051 A * | 10/1999 | Luckman et al. | ................ | 606/88 |
| 6,056,751 A | 5/2000 | Fenton, Jr. | | |
| 6,106,545 A | 8/2000 | Egan | | |
| 6,174,324 B1 | 1/2001 | Egan et al. | | |
| 6,217,591 B1 | 4/2001 | Egan et al. | | |
| 6,286,746 B1 | 9/2001 | Egan et al. | | |
| 6,358,271 B1 | 3/2002 | Egan et al. | | |
| 6,409,743 B1 | 6/2002 | Fenton, Jr. | | |
| 6,666,877 B2 | 12/2003 | Morgan et al. | | |
| 6,669,705 B2 | 12/2003 | Westhaver et al. | | |
| 6,923,824 B2 | 8/2005 | Morgan et al. | | |
| 6,984,237 B2 | 1/2006 | Hatch et al. | | |
| 7,090,111 B2 | 8/2006 | Egan et al. | | |
| 7,331,968 B2 * | 2/2008 | Arp et al. | ....................... | 606/142 |
| 2005/0277952 A1* | 12/2005 | Arp et al. | ....................... | 606/142 |

FOREIGN PATENT DOCUMENTS

WO    WO 2006/093975 A2    9/2006

OTHER PUBLICATIONS

PCT International Search Report—(PCT/US2008/007856) Date of Mailing Oct. 3, 2008.

* cited by examiner

*Primary Examiner* — Vy Q Bui (74) *Attorney, Agent, or Firm* — Faegre Baker Daniels LLP (57) ABSTRACT

An instrument is disclosed including: a top jaw member extending between a proximal end and a distal end and including a first top anchor target slot and a second top anchor target slot; a bottom jaw member extending between a proximal end and a distal end and including a first bottom anchor target slot and a second bottom anchor target slot; and a joint member connected to the proximal ends of the top jaw member and the bottom jaw member.

25 Claims, 11 Drawing Sheets

Fig. 5

DOUBLE ROW FIXATION SYSTEM, MEDIAL ROW ANCHOR PLACEMENT SYSTEM

RELATED APPLICATION(S)

The present application claims benefit of U.S. Provisional Application Ser. No. 60/946,012, filed Jun. 25, 2007, the contents of which are incorporated by reference herein in their entirety.

BACKGROUND

When soft tissue tears away from bone, reattachment becomes necessary. Various devices, including sutures alone, screws, staples, wedges, and plugs have been used in the past to secure soft tissue to bone.

Recently, various types of threaded suture anchors have been developed for this purpose. Some threaded suture anchors are designed to be inserted into a pre-drilled hole. Other suture anchors are self-tapping.

In repair of tissue attachments to bone, e.g. in the shoulder, techniques have been developed that vastly increase the repaired tissue to bone area resulting in a repair that more closely replicates the original structure. These repair techniques are commonly referred to as "double row fixation" and includes the typical edge repair location as well as an additional "medial row" of fixation using an additional, medially located (relative to the edge repair) set of suture anchors to secure tissue to bone.

Correct placement of the additional tissue anchors medial to the edge repair is often critical to the success of this repair technique. If the medial anchors are placed too medial in relation to the first row (i.e. too far medially inward from the tissue edge) damage can occur to the humeral head. Additionally, the relative placement of anchors is important. If the anchors are placed too close or far apart from each other, the strength of the repair may not add value to the overall reconstruction at the repair site.

SUMMARY

The inventors have realized that one may facilitate proper placement of suture anchors, e.g. medial row anchors in a "double row" repair. A "paddle style" grasper is structured to allow a desired depth of tissue bite while the width of the paddles are configured in such a way as to allow for fixation points to ideally spaced. With the grasper properly placed on the tissue, "punch through" suture anchors are deployed at the at "anchor targets" on the grasper paddles. A "punch tip" on the anchors pierce the tissue grasped by the grasper and penetrate, e.g., thread into adjacent bone tissue. With the anchors properly placed the grasper is removed, and sutures from the two anchors are attached to one another forming, e.g. a mattress style stitch to secure the tissue to the bone.

In one aspect, an instrument is disclosed including: a top jaw member extending between a proximal end and a distal end and including a first top anchor target slot and a second top anchor target slot; a bottom jaw member extending between a proximal end and a distal end and including a first bottom anchor target slot and a second bottom anchor target slot; and a joint member connected to the proximal ends of the top jaw member and the bottom jaw member.

In some embodiments, the top and bottom jaw members, in an open position, define an area for receiving a portion of tissue, and the joint member articulates the jaw members from the open position to a tissue engaging position where the top and bottom jaw members grasp the portion of tissue.

In some embodiments, the jaw members are in the tissue engaging position, the first top anchor slot and first bottom anchor slot are adapted to receive a first anchor extending into the first top anchor slot, through the portion of tissue, and out of the first bottom anchor slot.

In some embodiments, the jaw members are in the tissue engaging position, the second top anchor slot and second bottom anchor slot are adapted to receive a second anchor extending into the second top anchor slot, through the portion of tissue, and out of the second bottom anchor slot.

In some embodiments, the top jaw member and bottom jaw member each include a paddle extending along a longitudinal axis between the proximal end of the jaw member and the distal end of the jaw member, the paddle further extending along a transverse axis, transverse to the longitudinal axis, extending between a first side and a second side of the paddle.

In some embodiments, the first top anchor slot includes an aperture formed in the first side of the top jaw member paddle; the second top anchor slot includes an aperture formed in the second side of the top jaw member paddle; the first bottom anchor slot includes an aperture formed in the first side of the bottom jaw member paddle; and the second bottom anchor slot includes an aperture formed in the second side of the bottom jaw member paddle.

In some embodiments, the first top anchor slot and second top anchor slot are positioned at points substantially equidistant from the proximal end of the top jaw member; and the first bottom anchor slot and second bottom anchor slot are positioned at points substantially equidistant from the proximal end of the bottom jaw member.

In some embodiments, when the jaw members are in the tissue engaging position, the first top anchor slot is substantially aligned with the first bottom anchor slot along an axis substantially orthogonal to the transverse and longitudinal axes of the top and bottom jaw member paddles, and the second top anchor slot is substantially aligned with the second bottom anchor slot along an axis substantially orthogonal to the transverse and longitudinal axes of the top and bottom jaw member paddles.

In some embodiments, the tissue engaging position consists of the open position. Some embodiments include an endoscopic assembly including a grasping instrument the type described above. The assembly further includes a handle; a controller mounted on the handle; and a stem operatively connecting the controller to the instrument to selectively articulate the jaw members.

Some embodiments include a surgical cannula surrounding at leas a portion of the stem or the instrument.

In another aspect, a surgical kit is disclosed including a first and a second suture anchor. Each anchor includes a rigid punch tip portion having a first end adapted to penetrate through tissue and into bone and second end; and a suture portion extending from the second end of the punch tip portion. The kit also includes a grasper including: a top jaw member extending between a proximal end and a distal end and including a first top anchor target slot and a second top anchor target slot; a bottom jaw member extending between a proximal end and a distal end and including a first bottom anchor target slot and a second bottom anchor target slot; a joint member connected to the proximal ends of the top jaw member and the bottom jaw member.

The top and bottom jaw members, in an open position, define an area for receiving a portion of tissue, and the joint member articulates the jaw members from the open position to a tissue engaging position where the top and bottom jaw members grasp the portion of tissue.

When the jaw members are in the tissue engaging position, the first top anchor slot and first bottom anchor slot are adapted to receive a first anchor extending into the first top anchor slot, through the portion of tissue, and out of the first bottom anchor slot; and the second top anchor slot and second bottom anchor slot are adapted to receive a second anchor extending into the second top anchor slot, through the portion of tissue, and out of the second bottom anchor slot.

In some embodiments, the first top anchor slot includes an aperture formed in the first side of the top jaw member paddle; the second top anchor slot includes an aperture formed in the second side of the top jaw member paddle; the first bottom anchor slot includes an aperture formed in the first side of the bottom jaw member paddle; and the second bottom anchor slot includes an aperture formed in the second side of the bottom jaw member paddle.

In some embodiments, the first top anchor slot and second top anchor slot are positioned at points substantially equidistant from the proximal end of the top jaw member; and the first bottom anchor slot and second bottom anchor slot are positioned points substantially equidistant from the proximal end of the bottom jaw member.

In some embodiments, when the jaw members are in the tissue engaging position, the first top anchor slot is substantially aligned with the first bottom anchor slot along an axis substantially orthogonal to the transverse and longitudinal axes of the top and bottom jaw member paddles, and the second top anchor slot is substantially aligned with the second bottom anchor slot along an axis substantially orthogonal to the transverse and longitudinal axes of the top and bottom jaw member paddles.

In some embodiments the kit includes an anchor driver configured to engage the second end of the punch tip portion of at least one of the first and second anchors and drive the punch tip through tissue grasped by the grasper and into a portion bone located adjacent the bottom jaw member.

In some embodiments, the punch tip portion of each of the suture anchors includes a threaded tip, and the anchor driver is adapted to rotate and drive the at least one of the first and second anchors to bore into the portion of bone.

In some embodiments, the kit includes a suture welder including: a suture holding element adapted to receive the suture portions of the first and second suture anchors and place the suture portions in proximity to each other, a welding element adapted to apply energy to areas of the suture portions to at least partially fuse the suture portions to each other.

In some embodiments, the welding element includes a heater adapted to heat the suture portions.

In some embodiments, the welding element includes an ultrasound unit adapted to apply ultrasound energy to the areas of the suture portions to at least partially fuse the suture portions to each other.

In some embodiments, the suture welder further includes a tensioner adapted to apply tension to the suture portions.

In another aspect a method for securing a portion of tissue to an adjacent portion of bone is disclosed including providing a first and a second suture anchor each including a rigid punch tip portion having a first end adapted to penetrate through tissue and into bone and second end; a suture portion extending from the second end of the punch tip portion. The method includes providing a grasper including: a top jaw member extending between a proximal end and a distal end and including a first top anchor target slot and a second top anchor target slot; a bottom jaw member extending between a proximal end and a distal end and including a first bottom anchor target slot and a second top anchor target slot; a joint member connected to the proximal ends of the top jaw member and the bottom jaw member. The top and bottom jaw members, in an open position, define an area for receiving a portion of tissue, and the joint member articulates the jaw members from the open position to a tissue engaging position where the top and bottom jaw members grasp the portion of tissue.

The jaw members are in the tissue engaging position, the first top anchor slot and first bottom anchor slot are adapted to receive a first anchor extending into the first top anchor slot, through the portion of tissue, and out of the first bottom anchor slot.

When the jaw members are in the tissue engaging position, the second top anchor slot and second bottom anchor slot are adapted to receive a second anchor extending into the second top anchor slot, through the portion of tissue, and out of the second bottom anchor slot.

The method further includes grasping the portion of tissue between the top and bottom jaw elements such that the bottom jaw element is adjacent the bone; positioning first and second anchors proximal the first and second top anchor slots, respectively; driving the punch tip portions of first and second anchors, respectively, through the first and second top anchor slot, through the tissue, through the first and second bottom anchor slots, and into the bone; removing the grasper; and attaching the suture portions of the first and second anchors to each other to secure the tissue to the bone.

In some embodiments attaching the suture portions of the first and second anchors to each other includes: placing the suture portions in proximity to each other; applying energy to the suture portions to at least partially fuse the suture portions to each other.

In some embodiments, attaching the suture portions of the first and second anchors to each other includes tensioning the suture portions to secure the tissue to the bone.

In some embodiments, the energy includes thermal energy.

In some embodiments, the energy includes heat energy.

In some embodiments, the tissue includes a portion of a rotator cuff.

In some embodiments, the bone includes a portion of a humerous bone head.

Various embodiments may include any of the features described above, alone or in combination.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A-3I illustrate the use of the paddle grasper to provide fixation of tissue to bone.

DETAILED DESCRIPTION

Figure 1:
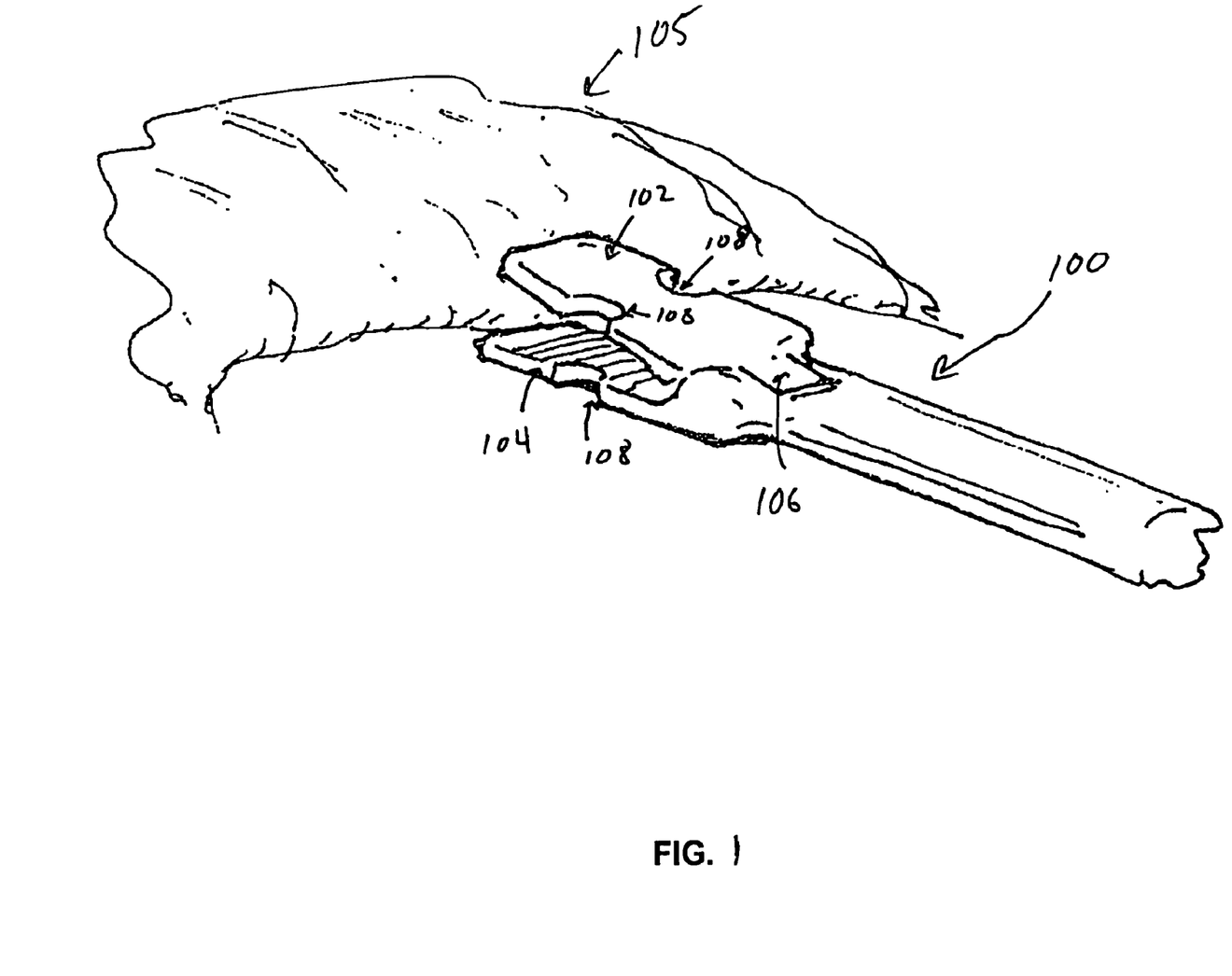
FIG. 1 is a perspective view of a paddle grasper.

Referring to FIG. 1, grasper 100 includes top jaw member 102 and bottom jaw member 104 connected by joint member 106. Jaw members 102, 104 open to receive a portion of tissue 105, e.g., a portion of rotator cuff tissue in a shoulder. Joint member 106 allows jaw members 102, 104 to engage and grasp the tissue located therebetween (e.g. by articulating jaws 102, 104 from an open position to a closed position, or simply by providing mechanical resistance as tissue is received between the jaw members).

As shown, the jaw members 102, 104 are flat, paddle type jaws. Jaw members 102, 104 each include a pair of anchor target slots 108. As described in further detail below, anchor target slots 108 can be used to easily and reliably provide desired positioning of suture anchors used to secure tissue 105 to bone 110.

Paddle 100 may be constructed of any suitable material, e.g. biocompatible material including metal (e.g. stainless steel), plastic, polymers, and or other materials.

Figure 2:
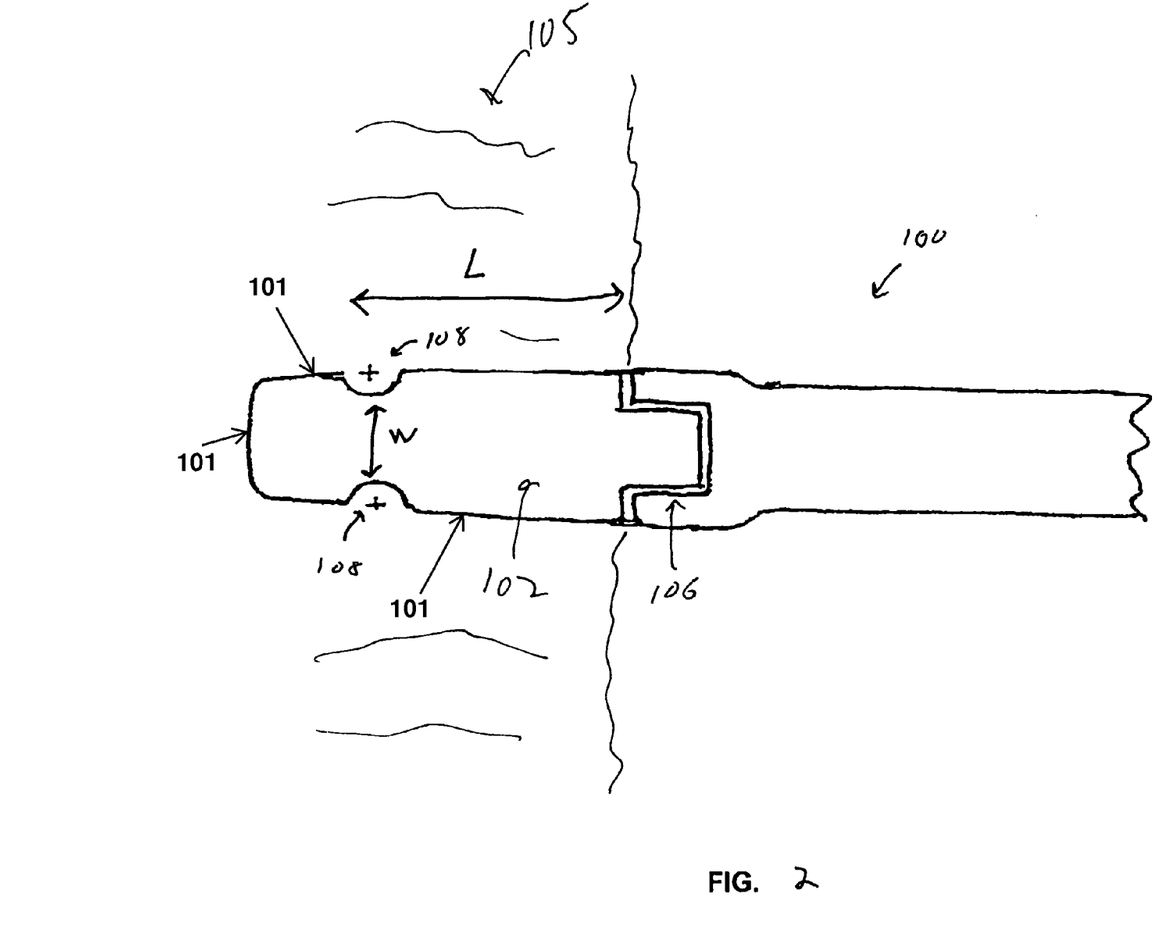
FIG. 2 is a top down view of the paddle grasped.

FIG. 2 shows a top down view of grasper 100 positioned to grasp tissue 105. Anchor target slots 108 are formed as aligned pair of, e.g., semicircular apertures in the sides (e.g. in the outer/perimeter edge 101) of the upper and lower jaw member paddles (Note that as used herein the term aperture indicates any open region through which a suture anchor may pass, and need not completely surround the anchor). The position of target anchor slots are chosen to correspond to a desired position for a pair of suture anchors 112. For example, as shown, target anchor slots 108 are placed such they are located a desired distance L from the edge of tissue 105 when the grasper has fully engaged the tissue. Accordingly, anchors 112 inserted at the target anchor locations will be placed at the correct distance medial the edge of tissue 105. Further anchor targets 108 are positioned distance W apart from each other on either side of jaw members 102, 104 Accordingly, anchors 122 inserted at the target anchor locations will be placed at the correct distance relative to each other. Of course, it is to be understood that other configurations may be used to provide any desired anchor placement.

Figure 3A:
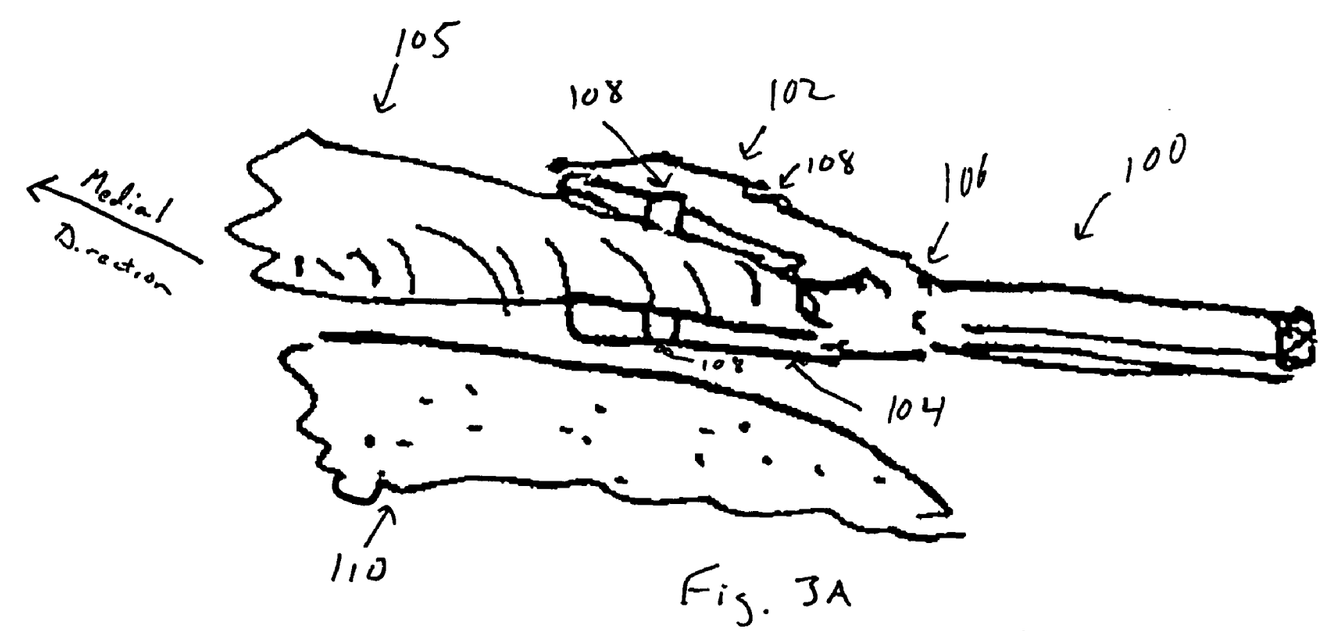
Figure 3B:
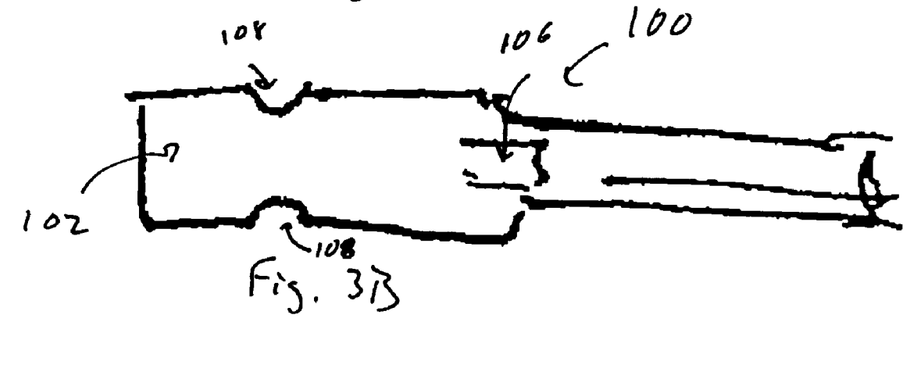

FIGS. 3A-3I illustrate the use of grasper 100 to secure rotator cuff tissue 105 to adjacent humerous head bone 110. Referring to FIG. 3A, grasper 100 receives tissue 105 between jaw members 102, 104 such that bottom jaw member 104 is adjacent to bone 110. The grasper is advanced as far as possible in the medial direction, filling the area between jaw members 102, 104 with tissue to provide the desired tissue "bite." A portion of tissue 105 is thereby grasped between jaw members 102, 104. FIG. 3B shows a top down view of grasper 100 corresponding to the perspective view shown in FIG. 3A.

Figure 3C:
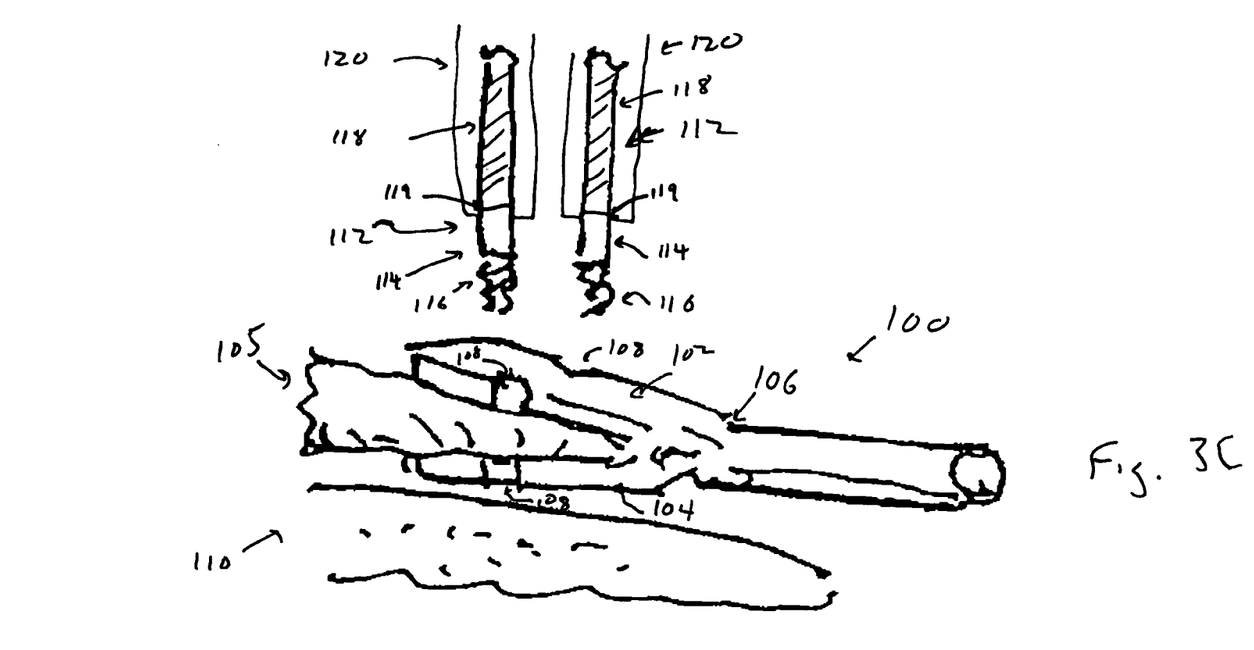
Figure 3D:
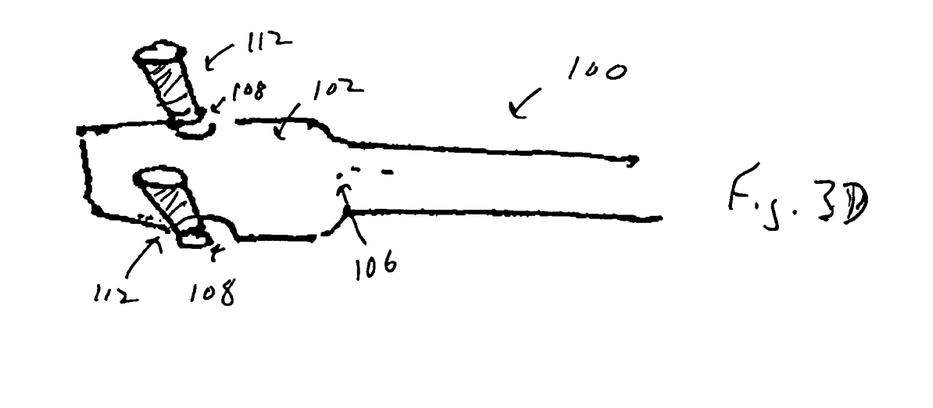

Referring to FIG. 3C, suture anchors 112 are positioned over anchor target slots 108. Suture anchors 112 each include a rigid (e.g. metal or rigid plastic) punch through portion 114 with a threaded tip 116. A flexible suture portion 118 extends from the end 119 of punch through portion 114 opposite threaded tip 116. Suture portions 118 may be made from any suitable suture material, including weldable (e.g. heat- or ultrasound-weldable) material. The ends 119 of punch through portions 114 are engaged by anchor drivers 120 (e.g. manual screw anchor driver, motorized anchor driver, etc.). FIG. 3D shows a top down view of grasper 100 corresponding to the perspective view shown in FIG. 3C.

Figure 3E:
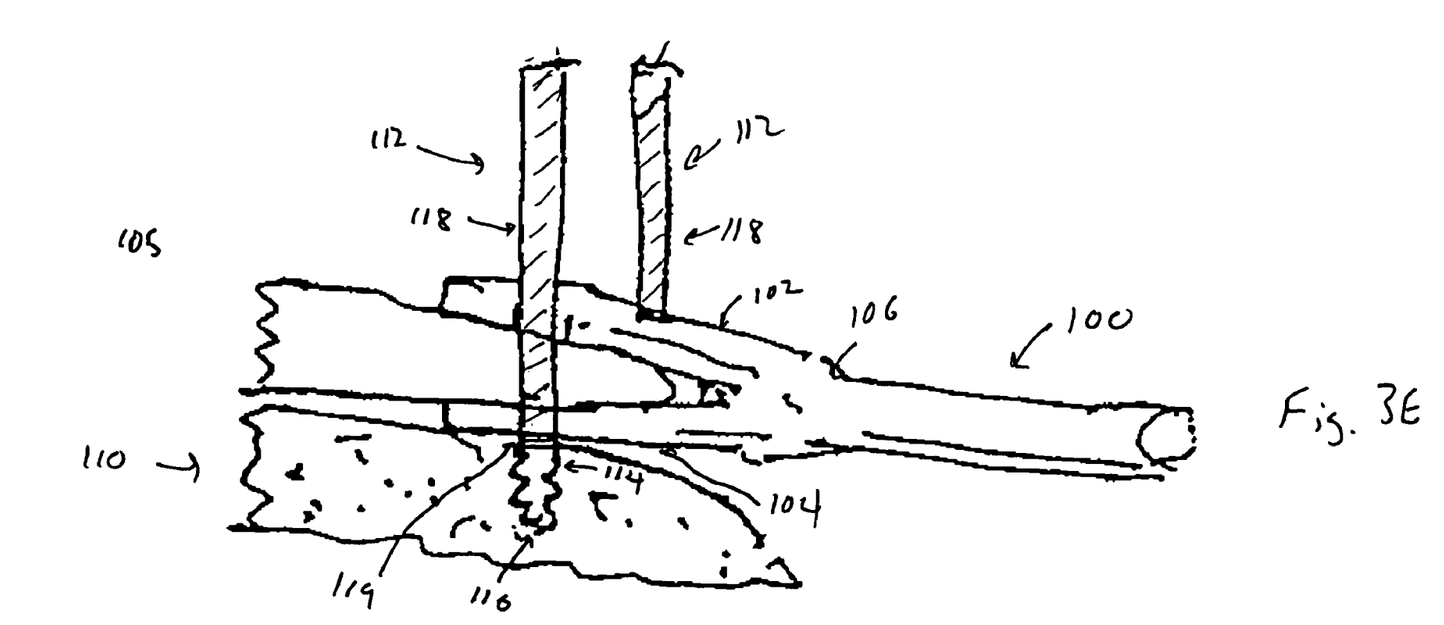

Referring to FIG. 3E, drivers 120 have been used to drive anchors 112 through tissue 105 and into bone 110, such that the rigid punch through portions 116 have penetrated (e.g. bored, treaded, augured, etc) into bone 110. Flexible suture portions 112 extend from the ends 119 of punch through portions 119 out through tissue 105. In the interest of clarity, anchor drivers 120 are not shown, but remain engaged with ends 119. In some embodiments, the driving of anchors 112 may be preceded by pre-drilling step when a drill is used to provide a guide hole into the tissue and bone.

Figure 3F:
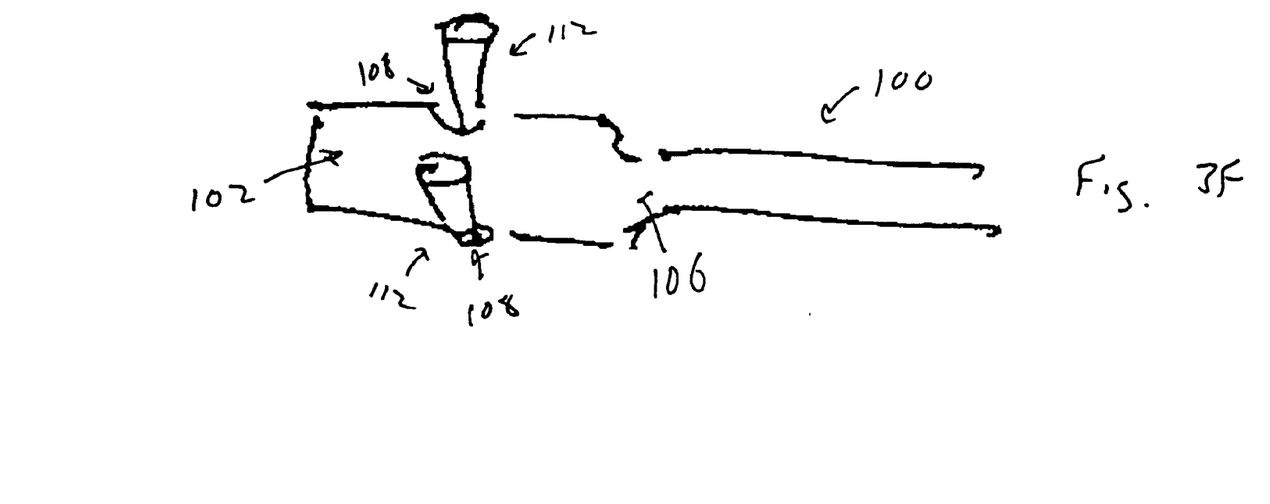

FIG. 3F shows a top down view of grasper 100 corresponding to the perspective view shown in FIG. 3E. Arrows indicate the rotation of anchor 112 by driver 120 to auger through tissue 105 and thread into bone 110.

Referring to FIG. 3G, grasper 100 has been removed, and anchor drivers 120 withdrawn from the treatment area. Punch through portions 114 of anchors 112 are securely anchored at the desired position (both relative to tissue 105 and each to each other) in bone 110. Flexible suture portions 118 extend from ends 119 of punch through portions 114, passing out through tissue 105.

Figure 3H:
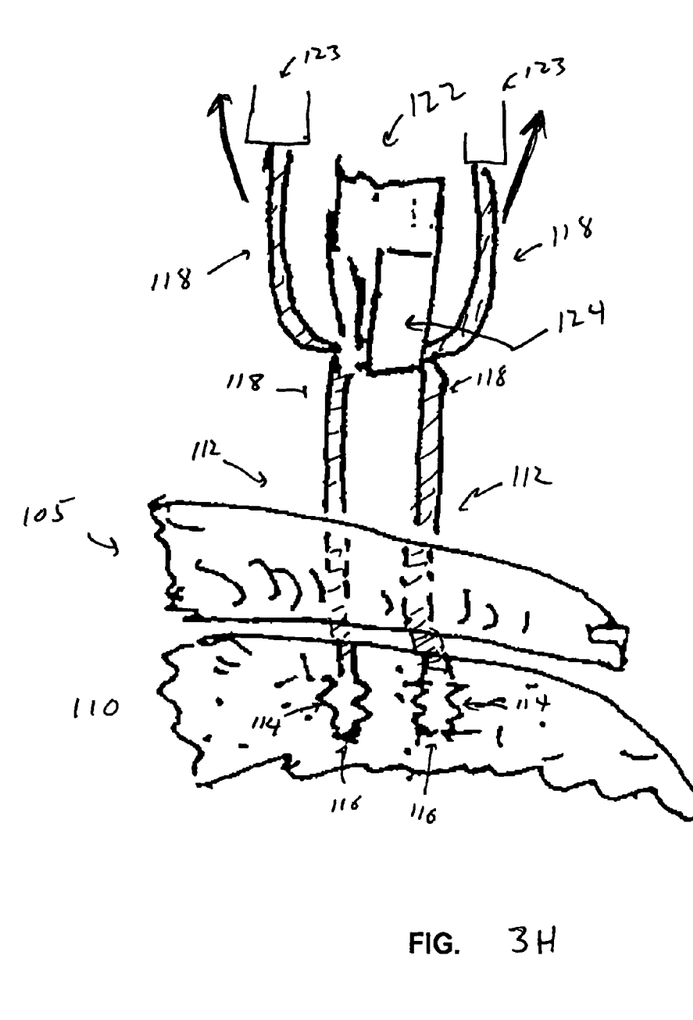

Referring to FIG. 3H, suture welder 122 engages flexible suture portions 118 extending from tissue 105. Welder 122 captures suture portions 118 in between welder jaws 124. Suture portions 118 are tensioned to secure tissue 105 to bone 110 (e.g. with a mattress style stitch or other suitable stitch known in the art). Welder 122 brings areas of flexible suture portions 118 into proximity with each other and applies energy (e.g. heat energy from a heating element, ultrasound energy from a ultrasound transducer, etc.) to fuse the areas together, thereby forming a knotless suture stitch connecting anchors 112 to each other to secure tissue 105 to bone 110. For example, tensioner 123 may apply tension in opposing directions to suture portions 118 (as indicated by dark arrows). It is to be understood that any other suitable technique for attaching anchors 112 may be used, including, for example, performing a conventional knotted stitch with flexible suture portions 118.

In various embodiments, welder 122 may be any suitable welder, e.g. of the types available from Axya Medical, Inc. of Beverly, Mass., including those described in, U.S. Pat. No. 7,090,111, issued Aug. 16, 2006, U.S. Pat. No. 6,923,824, issued Aug. 2, 2005, U.S. Pat. No. 6,669,705, issued Dec. 30, 2003, U.S. Pat. No. 6,666,877, issued Dec. 23, 2003, U.S. Pat. No. 6,409,743, issued Jun. 25, 2002, U.S. Pat. No. 6,358,271, issued Mar. 19, 2002, U.S. Pat. No. 6,286,746, issued Sep. 11, 2001, U.S. Pat. No. 6,217,591, issued Apr. 17, 2001, U.S. Pat. No. 6,174,324, issued Jan. 16, 2001, U.S. Pat. No. 6,106,545, issued Aug. 22, 2000, U.S. Pat. No. 6,056,751, issued May 2, 2000, U.S. Pat. No. 5,964,765, issued Oct. 12, 1999, and U.S. Pat. No. 5,893,880, issued Apr. 13, 1999 the contents of each of which are incorporated by reference herein in their entirety.

FIG. 3I shows welder 122 retracted from the area after the formation of knotless stitch 126. Note that by employing grasper 120, proper placement of anchors 112 was easily accomplished. The above steps may be repeated to deliver additional anchors.

Note that while the above examples show a grasper 100 featuring paddle type jaw members 102, 014 each having a pair of anchor target slots 108, any suitable jaw shape featuring and number of anchor target slots may be used. For a given embodiment, placement of the anchor target slots is determined by the desired positioning of the anchors to be implanted.

Figure 4:
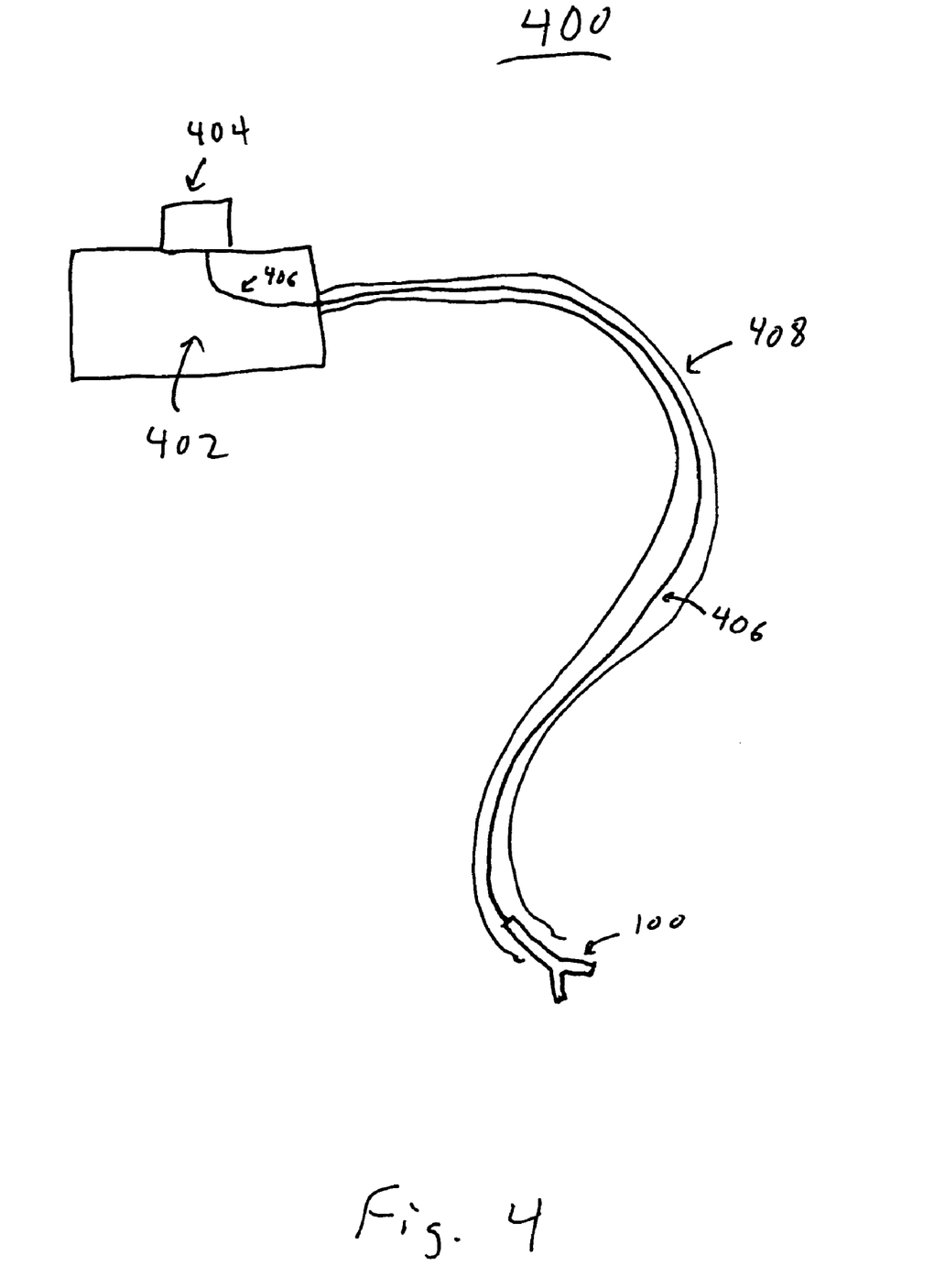
FIG. 4 is a schematic of an endoscopic system featuring the paddle grasper.

Referring to FIG. 4, in some embodiments grasper 100 is incorporated in endoscopic system 400. Endoscopic system 400 includes handle 402 with a controller 404. Stem 406 connects controller 404 to grasper 100, allowing an operator to articulate grasper 100 (e.g. to advance, retract, rotate, etc. grasper 100, or to articulate jaws 102, 104 to engage tissue 105). Grasper 100 and stem 406 are contained in a surgical cannula 408 or other tube which can be inserted into the patient through a small incision. In various embodiments, endoscopic system 400 may include any of the various features or devices familiar in the art of endoscopic surgery.

Figure 5:
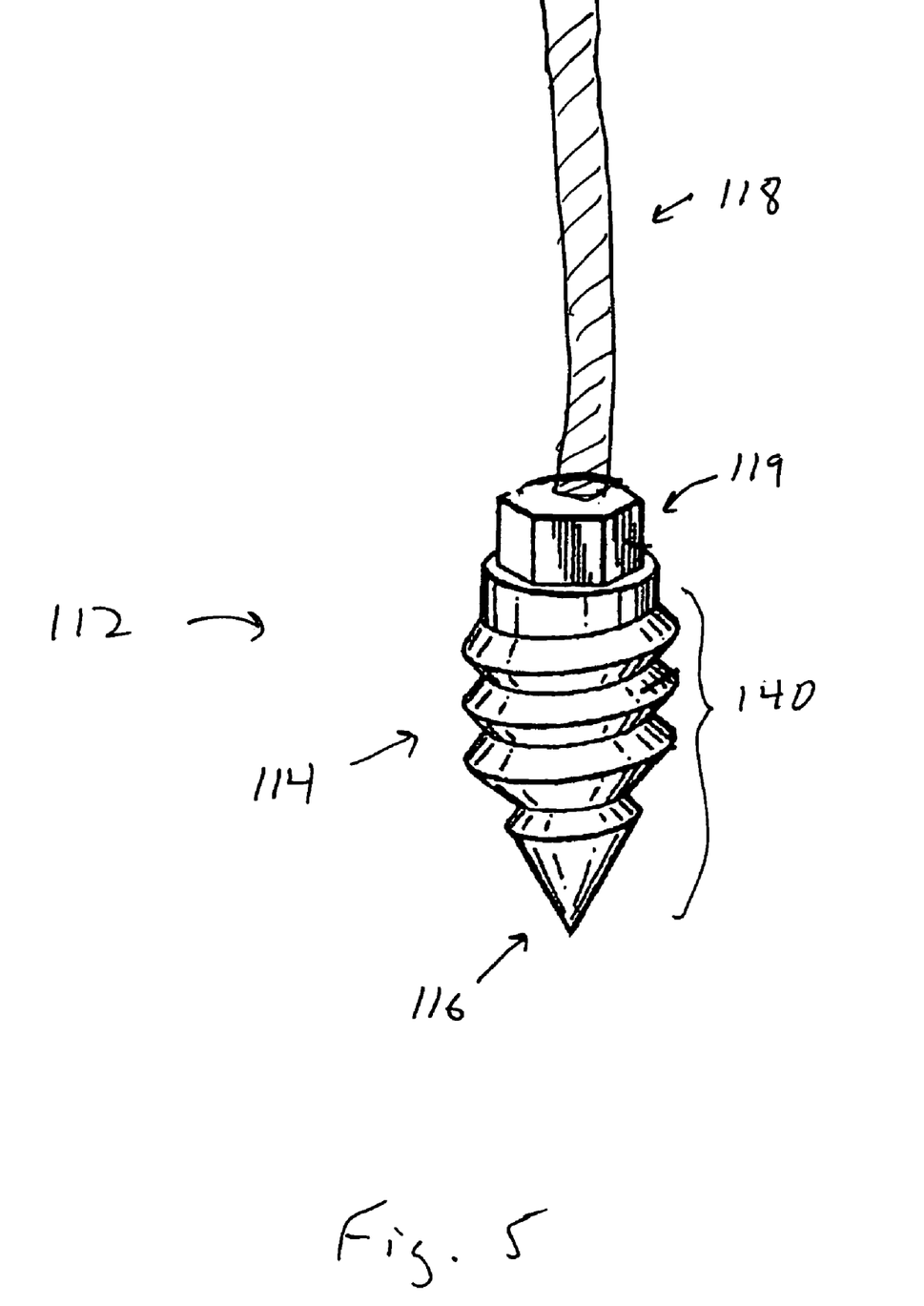
FIG. 5 shows an exemplary suture anchor.

As illustrated in FIG. 5, in one embodiment, one suture anchor 112 includes an elongated rigid punch through portion 114 which extends along a longitudinal axis between end 119 and threaded tip end 116. End 119 includes a drive head (e.g. as shown a hexagonal drive head) for engagement with driver 120. End 116 includes a threaded portion 140 for auguring, boring, etc. through bone and tissue.

Anchor 112 includes flexible suture portion 118 extending from end 119, and secured to punch through portion 114. Suture portion 118 may be made of a material amenable to bonding through the application of heat or energy thereto such as, for example, nylon (polyamide), polypropylene, Dacron® (polyester), polyglycolic acid (PGA), polyglyconate, and polydioxanone. In some embodiments, rigid punch through portion 114 may also be made of such material. In such cases portion 114 may be bonded to portion 118 by the application by the application of heat or other energy (e.g. ultrasound energy). Other suitable methods of bonding can be used if for example, portion 114 is made of another material, such as stainless steel, titanium, or some other durable, non-degradable, biocompatible material.

The suture anchor 112 or parts thereof can be made of a bioresorbable material which will be resorbed after residing in a patient.

Figure 6A:
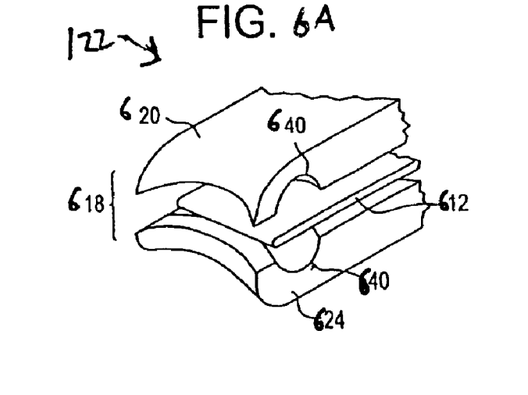
FIGS. 6A and 6B show an exemplary suture welder.
Figure 6B:
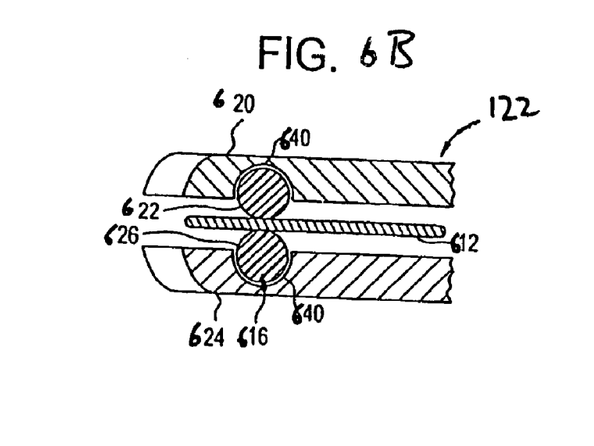

FIGS. 6A and 6B show an embodiment of suture welder 122 for creating fused stitch. The suture welder 122 includes a jaw assembly 618 having a first jaw 620 for receiving a first suture segment 622 in recess 640, and a second jaw 624 for receiving a second suture segment 626 in recess 640 so that the second suture segment is adjacent the first suture segment. The suture welder 122 also includes a heater element 612 positioned between the suture segments 622, 626. The heater element 612 is adapted to melt at least adjacent surfaces of the overlapping first and second suture segments 622, 626. Once melted, the suture segments 622, 626 can be pressed together by the jaws 620, 624 and allowed to cool to form a fused layer 28 to secure the suture segments 622, 626 together.

The suture welder 122 beneficially provides a fused stitch 14 an elongated material, such as a surgical suture 616, wherein the stitch has at least comparable strength to knotted stitches or loops closed by other means. The fused stitch gains its comparable strength from the properties of the fused layer of the stitch, as detailed more fully in U.S. Pat. No. 5,893,880, which is assigned to the assignee of the present disclosure and incorporated herein by reference.

In particular, the fused stitch is formed through a welding process in which portions of the suture segments are locally heated through the application of heat thereto until opposing portions melt. The melted portions are then pressed together in an overlapped joint and become fused. The joint includes a fused layer between and joining the first and second suture segments. The fused layer is fused material from the first and second suture segments and preferably is relatively thin and has a relatively large shear area compared to the suture segments. In some embodiments, the suture welder 122 facilitates the creation of such a fused portion by maximizing contact between the suture segments during welding.

The fused stitch produced by the suture welder 122 comprises one or more pieces of an elongated material, such as a surgical suture, or other material which is amenable to bonding through the application of heat thereto. Suitable materials for the elongated material include polymers, especially thermoplastic materials such as, for example, nylon (polyamide), polypropylene, DACRON®. (polyester), polyglycolic acid (PGA), polyglyconate, and polydioxanone. The elongated material can be made of a single strand of a substantially monofilamentous material, or it can comprise multiple strands forming a single suture. The multi-strands can be twisted, braided or otherwise interlinked to increase the density, and thus the strength, of the composite strand.

As noted above, in some embodiments, welder 122 may produce fused stitch 126 from suture portions 118 by applying other types of energy including ultrasound energy, radio frequency energy, chemical energy, optical energy, etc.

The techniques and devices disclosed herein may be used to fixate any suitable tissue to bone, including, but not limited to, muscle tissue, tendons, and ligaments.

The techniques and devices disclosed above may be used in treating human patients, veterinary patients, etc.

In the event that any technical definitions presented in this application conflict with any documents incorporated by reference, the definition found in the present application should be understood to hold.

While particular examples have been provided above, it will be understood by those skilled in the art that various changes in form and details may be made therein without departing from the scope of the claims.

What is claimed is:

1. An instrument comprising:
   a top jaw member extending between a proximal end and a distal end and comprising a first top anchor target slot and a second top anchor target slot;
   a bottom jaw member extending between a proximal end and a distal end and comprising a first bottom anchor target slot formed in an outer edge of the bottom jaw member and a second bottom anchor target slot formed in the outer edge of the bottom jaw member; and
   a joint member connected to the proximal ends of the top jaw member and the bottom jaw member;
   wherein the top and bottom jaw members, in an open position, define an area for receiving a portion of tissue, and the joint member articulates the jaw members from the open position to a tissue engaging position wherein the top and bottom jaw members grasp the portion of tissue;
   wherein, when the jaw members are in the tissue engaging position, the first top anchor slot and first bottom anchor slot are adapted to receive a first anchor extending into the first top anchor slot, through the portion of tissue, and out of the first bottom anchor slot; and
   wherein, when the jaw members are in the tissue engaging position, the second top anchor slot and second bottom anchor slot are adapted to receive a second anchor extending into the second top anchor slot, through the portion of tissue, and out of the second bottom anchor slot.

2. The instrument of claim 1, wherein the top jaw member and bottom jaw member each comprise a paddle extending along a longitudinal axis between the proximal end of the jaw member and the distal end of the jaw member, said paddle further extending along a transverse axis, transverse to said longitudinal axis, extending between a first side and a second side of the paddle.

3. The instrument of claim 2, wherein the first top anchor slot comprises an aperture formed in the first side of the top jaw member paddle; the second top anchor slot comprises an aperture formed in the second side of the top jaw member paddle; the first bottom anchor slot comprises an aperture formed in the first side of the bottom jaw member paddle; and the second bottom anchor slot comprises an aperture formed in the second side of the bottom jaw member paddle.

4. The instrument of claim 3, wherein the first top anchor slot and second top anchor slot are positioned at points substantially equidistant from the proximal end of the top jaw member; and the first bottom anchor slot and second bottom anchor slot are positioned at points substantially equidistant from the proximal end of the bottom jaw member.

5. The instrument of claim 4, wherein, when the jaw members are in the tissue engaging position; the first top anchor slot is substantially aligned with the first bottom anchor slot along an axis substantially orthogonal to the transverse and longitudinal axes of the top and bottom jaw member paddles; and the second top anchor slot is substantially aligned with the second bottom anchor slot along an axis substantially orthogonal to the transverse and longitudinal axes of the top and bottom jaw member paddles.

6. The instrument of claim 1, wherein the tissue engaging position consists of the open position.

7. An endoscopic assembly including the instrument of claim 1, and further comprising: a handle; a controller mounted on the handle; a stem operatively connecting the controller to the instrument to selectively articulate the jaw members.

8. The endoscopic assembly of claim 7, further comprising a surgical cannula surrounding at least a portion of the stem or the instrument.

9. The instrument of claim 1, wherein the first bottom anchor target slot and second bottom anchor target slot are formed in the outer edge of the bottom jaw member on opposite sides of a longitudinal axis of the bottom jaw member.

10. The instrument of claim 9, wherein the first top anchor target slot is formed in an outer edge of the top jaw member and the second top anchor target slot is formed in the outer edge of the top jaw member.

11. The instrument of claim 10, wherein the first top anchor target slot and second top anchor target slot are formed in the outer edge of the top jaw member on opposite sides of a longitudinal axis of the top jaw member.

12. The instrument of claim 1, wherein the first top anchor target slot is formed in an outer edge of the top jaw member and the second top anchor target slot is formed in the outer edge of the top jaw member.

13. The instrument of claim 12, wherein the first top anchor target slot and second top anchor target slot are formed in the outer edge of the top jaw member on opposite sides of a longitudinal axis of the top jaw member.

14. The instrument of claim 1, wherein the first top anchor target slot and second top anchor slot are semicircular.

15. An instrument comprising:
a top jaw member extending between a proximal end and a distal end and comprising a first top anchor target slot and a second top anchor target slot;
a bottom jaw member extending between a proximal end and a distal end and comprising a first bottom anchor target slot formed in a perimeter edge of the bottom jaw member and a second bottom anchor target slot formed in the perimeter edge of the bottom jaw member; and
a joint member connected to the proximal ends of the top jaw member and the bottom jaw member;
wherein the top and bottom jaw members, in an open position, define an area for receiving a portion of tissue, and the joint member articulates the jaw members from the open position to a tissue engaging position wherein the top and bottom jaw members grasp the portion of tissue;
wherein, when the jaw members are in the tissue engaging position, the first top anchor slot and first bottom anchor slot are adapted to receive a first anchor extending into the first top anchor slot, through the portion of tissue, and out of the first bottom anchor slot; and
wherein, when the jaw members are in the tissue engaging position, the second top anchor slot and second bottom anchor slot are adapted to receive a second anchor extending into the second top anchor slot, through the portion of tissue, and out of the second bottom anchor slot; and
wherein the first top anchor slot is independent of the second top anchor slot, and wherein the first bottom anchor slot is independent of the second bottom anchor slot.

16. The instrument of claim 15, wherein the top jaw member and bottom jaw member each comprise a paddle extending along a longitudinal axis between the proximal end of the jaw member and the distal end of the jaw member, said paddle further extending along a transverse axis, transverse to said longitudinal axis, extending between a first side and a second side of the paddle.

17. The instrument of claim 16, wherein the first top anchor slot comprises an aperture formed in the first side of the top jaw member paddle; the second top anchor slot comprises an aperture formed in the second side of the top jaw member paddle; the first bottom anchor slot comprises an aperture formed in the first side of the bottom jaw member paddle; and the second bottom anchor slot comprises an aperture formed in the second side of the bottom jaw member paddle.

18. The instrument of claim 17, wherein the first top anchor slot and second top anchor slot are positioned at points substantially equidistant from the proximal end of the top jaw member; and the first bottom anchor slot and second bottom anchor slot are positioned at points substantially equidistant from the proximal end of the bottom jaw member.

19. The instrument of claim 15, wherein, when the jaw members are in the tissue engaging position; the first top anchor slot is substantially aligned with the first bottom anchor slot along an axis substantially orthogonal to the transverse and longitudinal axes of the top and bottom jaw member paddles; and the second top anchor slot is substantially aligned with the second bottom anchor slot along an axis substantially orthogonal to the transverse and longitudinal axes of the top and bottom jaw member paddles.

20. The instrument of claim 15, wherein the tissue engaging position consists of the open position.

21. The instrument of claim 15, wherein the first bottom anchor target slot and second bottom anchor target slot are formed in the perimeter edge of the bottom jaw member on opposite sides of a longitudinal axis of the bottom jaw member.

22. The instrument of claim 21, wherein the first top anchor target slot is formed in an perimeter edge of the top jaw member and the second top anchor target slot is formed in the perimeter edge of the top jaw member.

23. The instrument of claim 22, wherein the first top anchor target slot and second top anchor target slot are formed in the perimeter edge of the top jaw member on opposite sides of a longitudinal axis of the top jaw member.

24. The instrument of claim 15, wherein the first top anchor target slot is formed in an perimeter edge of the top jaw member and the second top anchor target slot is formed in the perimeter edge of the top jaw member.

25. The instrument of claim 24, wherein the first top anchor target slot and second top anchor target slot are formed in the perimeter edge of the top jaw member on opposite sides of a longitudinal axis of the top jaw member.

* * * * *